United States Patent [19]

Rubenstein et al.

[11] 4,130,462

[45] * Dec. 19, 1978

[54] RECEPTOR STERIC HINDRANCE IMMUNOASSAY FOR RECEPTOR DETERMINATION

[75] Inventors: Kenneth E. Rubenstein, Menlo Park; Richard K. Leute, Mountain View, both of Calif.

[73] Assignee: Syva Company, Palo Alto, Calif.

[ * ] Notice: The portion of the term of this patent subsequent to Jan. 27, 1993, has been disclaimed.

[21] Appl. No.: 751,805

[22] Filed: Dec. 16, 1976

[51] Int. Cl.² ............... G01N 31/14; A61K 39/00; A61K 43/00

[52] U.S. Cl. .................. 195/103.5 A; 23/230 B; 424/1; 424/12

[58] Field of Search ............ 195/103.5 A; 424/1, 424/12; 23/230 B

[56] References Cited

U.S. PATENT DOCUMENTS 3,935,074  1/1976  Rubenstein et al. .............. 424/12

OTHER PUBLICATIONS

Scharpe et al., Clin. Chem. 22/6, (1976) pp. 733-738.

*Primary Examiner*—Alven E. Tanenholtz
*Assistant Examiner*—C. A. Fan
*Attorney, Agent, or Firm*—Townsend and Townsend

[57] ABSTRACT

A method is provided for the determination of receptors, particularly antibodies, where a polyepitopic reagent is employed, at least one of the epitopes being specific for the receptor of interest. The epitopic sites are situated on the reagent, so that the binding of the receptor of interest to the reagent will sterically hinder binding of receptors other than the receptor of interest.

In carrying out the assay, the sample suspected of containing the receptor of interest, the reagent, and a predetermined amount of receptors for the other epitopes are combined. Because of the steric inhibition to the simultaneous binding of the two different receptors, the amount of receptor of interest bound to the reagent will affect the amount of the other receptor which becomes bound to the reagent. By analyzing directly or indirectly for the amount of the receptor which is added in a predetermined amount, and comparing the results to known standards, qualitative or quantitative determinations of the amount of receptor of interest may be made. Various detector systems may be employed for determining the amount of the receptor of interest which is present in the unknown sample. The systems include stable free radicals, enzymes, radioactive labels, fluorescers, and the like.

13 Claims, No Drawings

RECEPTOR STERIC HINDRANCE IMMUNOASSAY FOR RECEPTOR DETERMINATION

BACKGROUND OF THE INVENTION

1. Field of the Invention

In many situations, it is desirable to determine the amount of a specific receptor which may be present in a physiological fluid. For many physiological compounds, there are specific receptors which will bind. For example, thyroxine is specifically bound by thyroxine binding globulin and thyroxine binding prealbumin. Certain steriods also have specific naturally occuring receptors. There is, therefore, an interest in being able to determine these receptors.

There is the further situation that for a wide variety of drugs and naturally occuring physiologically effective materials, methods of determination have been evolved which require the use of antibodies. With haptens, for example, the hapten is conjugated to an antigen and then injected into an animal. After harvesting of the antibodies, it is necessary to be able to determine the antibody titer and binding constant. For this purpose, it is necessary to have an accurate sensitive method to measure the amount of antibody which is specific for the hapten or antigen of interest.

Finally, for certain diseases e.p. syphilis, one can determine the presence of the microorganism by assaying for antibodies to the microorganism. It is found in these instances that there can be simple compounds which will bind specifically to the antibodies to the organism. This technique then affords a method for determining the antibodies to the organism in the physiological fluid.

2. Description of the Prior Art

U.S. Pat. No. 3,935,074 describes a technique for determining ligands employing steric hindrance between antibodies. See also the reference cited therein. See also Abstracts of a Symposium-Enzymes General V, Items 2028 and 2029, Carrico, et al (1976); Carrico, et al Anal. Biochem. 72 271 (1976); and Schroeder, et al, ibid 72 7283 (1976).

SUMMARY OF THE INVENTION

The subject invention provides a method for determining naturally occuring receptors, particularly antibodies. The method involves employing a polyepitopic reagent having epitopic sites specific for the receptor of interest, as well as other (foreign) epitopic sites which do not bind to the receptor of interest. In addition, the presence of antibodies as to one group of epitopic sites inhibits the simultaneous binding of receptors to the other group of epitopic sites. Various techniques may be employed for determining the amount of receptor of interest which is present. Common detector molecules can be employed in the reagent as foreign epitopes conjugated to the ligand for the receptor of interest, so that the receptor for the detector molecule and the detector group are the same in assaying for receptors having a wide variety of specificity.

DESCRIPTION OF THE SPECIFIC EMBODIMENTS

The subject assay is predicated on the ability to provide a molecule which has at least two different epitopic sites which are spatially situated in the molecule so that receptors to the molecule are sterically inhibited from being simultaneously bound to the two groups of epitopic sites. The first group of epitopic sites, which may be one or more epitopic sites, will be specific for a receptor of interest, normally naturally occuring receptors and antibodies. The second group of epitopic sites, which may be one epitopic site, is involved with the functional group which is part of the detection scheme.

When receptor of interest is present in the unknown, it will bind to the reagent, so as to sterically inhibit binding of the other receptor involved in the detection system. By measuring the amount of receptor involved in the detection system which remains unbound, one can relate this value to the amount of receptor of interest which was present in the sample. Various detection schemes can be employed for determining the amount of bound or unbound receptor involved in the detection scheme. These techniques will normally employ chemical and/or physical methods for obtaining an electromagnetic signal.

Definitions

Whenever used in this specification, the following terms will have the meaning indicated.

Primary Receptor — a macromolecule, normally a polypeptide, polysaccharide or nucleic acid, usually polypeptides, and most frequently antibodies.

Secondary Receptor — the secondary receptor will normally be a polypeptide, most usually an antibody, and is involved with the detection system.

Receptor — A macromolecule which is capable of recognizing a specific spatial and polar conformation by binding to such conformation substantially exclusively.

Epitopes — that portion of a molecule which is specifically recognizable by a receptor, normally an antibody. It is also referred to as the determinant site.

Reagent — a molecule having two different groups of epitopes, each group being recognizable by different receptors. The first group is recognizable by the Primary Receptor, the receptor which is being assayed. The second group of epitopic sites is associated with the Secondary Receptor, which is involved with the assay method. The two groups of epitopic sites are spatially juxtaposed so as to sterically inhibit simultaneous binding of the two groups of receptors to the reagent. Inhibition need not be complete inhibition, it being sufficient that a substantial proportion of the receptors of the other group are prevented from binding.

Detectant — the means employed, including any chemical reagents, for determining the amount of bound or unbound Secondary Receptor. There will be two primary means involved.

The first means has a detector ligand which gives a a different electromagnetic signal when subjected to electromagnetic radiation, depending upon whether the detector ligand is bound to Secondary Receptor or unbound, e.g. a fluorescing molecule.

The second means will employ a Detector Molecule which is capable of binding to the Secondary Receptor.

Ligand — a molecule having an epitopic site recognizable by the Primary Receptor. The molecule will be either antigenic or haptenic.

Ligand Analog — a group having at least one epitope common to the ligand and normally differing from the ligand by removal of a hydrogen atom and replacement by a bond or linking group, so that the ligand analog is recognizable by the Primary Receptor.

Detector Ligand — the portion of the reagent which contains the detector epitope. The group is bonded to the ligand analog by a bond or linking group. The same or substantially the same group will normally be present in the molecule employed as the Detector Molecule.

In the subsequent discussion, the term antibodies will be employed as exemplary of receptors, since antibodies will be the most common receptor of interest. However, other receptors, either as Primary or Secondary Receptors may be involved, particularly naturally occurring receptors, enzymes, cells, and the like. Where different considerations are involved for antibodies as compared to other receptors, a specific comment will be made.

ASSAY

The subject assay is carried out in an aqueous medium at a moderate pH, generally close to the pH for optimum binding of the antibody to ligand, by combining a sample suspected of containing Primary Receptor, Reagent, Secondary Receptor, and ancillary reagents necessary for the Detectant. By employing a Detectant, the amount of Secondary Receptor (anti(detector ligand)) which is bound and/or unbound to the Detector Ligand portion of the Reagent is determined. Because of the steric inhibition of simultaneous binding of Primary Receptor and Secondary Receptor to the Reagent, the amount of bound and/or unbound Secondary Receptor will be related to the amount of Primary Receptor which is present in the medium.

Where the Reagent has a plurality of epitopes common to the ligand and a plurality of epitopes common to the Detector Ligand, simultaneous binding of antibody to the two different epitopes can occur, except where the two different epitopes are sufficiently close together. Therefore, in referring to the steric inhibition of simultaneous binding of the two different antibodies, where a molecule has a plurality of epitopes common to the two different antibodies, the reference is to pairs of epitopes which provide the necessary steric inhibition, and not to the molecule as a whole.

The assay is concerned with available sites for binding of the Secondary Receptor to Reagent. To the extent that all, or substantially all of the Reagent present in the assay medium is bound to Primary Receptor, the Secondary Receptor will be precluded or substantially precluded from binding to Reagent. The more Primary Receptor present, the less the amount of Secondary Receptor which may bind to Reagent. Therefore, the amount of Reagent bound to Secondary Receptor is related to the amount of Primary Receptor present in the assay medium.

In carrying out the assay, an aqueous medium will normally be employed. Other polar solvents may also be employed, ususally oxygenated organic solvents of from 1 to 6, more usually from 1 to 4 carbon atoms, including alcohols, ethers, and the like. Usually, these co-solvents will be present in less than about 20 weight percent, more usually in less than about 10 weight percent.

The pH for the medium will usually be in the range of about 5 to 10, more usually in the range of about 6 to 9. Various buffers may be used to achieve the desired pH and maintain it during the determination. Illustrative buffers include borate, phosphate, carbonate, Tris, barbital, and the like. The particular buffer employed is not critical to this invention, but in particular assays, one buffer may be preferred over another.

Moderate temperatures are normally employed for carrying out the assay and usually constant temperatures during the period of the assay will be employed. The temperatures normally range from 15° to 50° C., more usually from about 20° to 40° C.

The concentrations of Primary Receptor (based on binding sites) which may be assayed will vary from about $10^{-4}$ to $10^{-15}$M, more usually from about $10^{-6}$ to $10^{-11}$M. Whether the assay is qualitative, semi-quantitative or quantitative, the particular detection technique and the concentration of Primary Receptor of interest will normally determine the concentration of the outer reagents. Normally, the concentration of Reagent will not exceed 10 times and more usually will be equal to or less than the maximum concentration of interest, but will be no less than $10^{-7}$, more usually not less than $10^{-4}$ of the minimum concentration of interest. The Secondary Receptor concentration will normally not be less than about one tenth, more usually will be equal to or up to about $10^7$ times the concentration of Reagent.

The order of addition may vary widely. It is normally desirable to have the binding of the Primary Receptor go substantially to completion under the assay conditions, followed by the addition of the Secondary Receptor. Preferably, the unknown sample may be combined with the Reagent, followed by the addition of the Secondary Receptor. Depending on the particular assay technique, the Detectant may now be employed.

In effect, one allows the amount of Primary Receptor present in the unknown to fill the available binding sites of the Reagent present in the assay medium. Depending on the conditions employed, the amount of time allowed for the immunological reaction to occur, and the order of addition, there will be differing amounts of unbound Reagent. To the mixture is now added Secondary Receptor, which will combine with Reagent which is not bound to Primary Receptor. By employing the appropriate Detectant, one can analyze for the amount of bound or unbound Secondary Receptor, which amount is related to the amount of Primary Receptor present in the sample.

The times between the various additions and immunological reactions will vary widely, depending on the particular Primary Receptors and complementary ligands involved, the mode of addition, the concentrations involved, the binding constants of the antibodies, and the like. Normally, times between additions may vary from a few seconds to many hours, usually not exceeding 12 hours, more usually not exceeding 6 hours. After adding each component to the assay mixture, different incubation periods before adding the next component or taking the measurement will be involved. Since the ultimate result will be dependent upon the result obtained with standards treated in substantially the same manner and, when possible, in the identical manner, the particular mode and periods of time are not critical, so long as the desired differentiation is obtained with varying concentrations of Ligand and the results are reproducible.

Depending on the choice of the assay, the equipment employed and the concentration of the Primary Receptor involved, assay volumes may be as small as about 1 μl, more usually at least 25 μl, and will usually not exceed 5ml, more usually not exceeding about 3ml.

With the exception of the electromagnetic radiation sensitive detector technique, the other detection techniques specifically described have been previously disclosed in the literature, with a few of the available references having been indicated previously. Therefore, as to these techniques which have been published, only a brief description of the method will be given.

In radioimmunoassay, the Detectant involves a detector molecule which is a radioactive analog of the Detector Ligand. After combining the unknown, Reagent, the Secondary Receptor and the radioactive analog, the bound radioactive analog may be separated from the unbound analog, by centrifugation, chromatography, solid support or the like. One or both of the resulting fractions containing the bound and unbound components can then be assayed for the amount of radioactive analog which is present.

In the spin label technique, the Detectant involves a detector molecule which is a spin labeled analog of the Detector Ligand. The assay mixture is taken up into an electron spin resonance cell and introduced into the cavity of an electron spin resonance spectrometer. The peak height may then be determined at one or more points in the spectrum.

In the enzyme technique, the Detectant involves a detector molecule which is an enzyme labeled analog of the Detector Ligand. The necesary substrates are introduced into the assay mixture, and the enzyme activity determined in accordance with the particular enzyme. For example, with a dehydrogenase, the spectral change occurring as a result of the reduction of nicotinamide adenine dinucleotide may be determined after a fixed period of time for a specified period of time, for example, after 5 minutes from the addition for a period of 2 minutes.

In the electromagnetic sensitive detector technique, the Detectant involves electromagnetic radiation, e.g. light, of an appropriate wavelength to be absorbed by the Detector Ligand. The sample is introduced into a spectrometer and absorption or emission of electromagnetic radiation is determined. With a fluorescing molecule, the sample is introduced into a fluorometer and irradiated with light at or near the absorption maximum of the fluorescer. The emission intensity is then determined. As will be discussed, the emission or absorption intensity will be a function of the amount of Detector Ligand bound to antibody.

MATERIALS

Primary Receptor for Ligand

The ligands to which the Primary Receptor specifically binds may vary widely, normally having a molecular weight of at least 110, more usually at least 125, with a maximum molecular weight unlimited, although usually not exceeding 10 million.

Among ligands which are drugs, will be compounds which act as narcotics, hyponotics, sedatives, analgesics, antipyretics, anesthetics, psychotogenic drugs, muscle relaxants, nervous system stimulants, anticholinesterase agents, parasympathomimetic agents, sympathomimetic agents, α-adrenergic blocking agents, antiadrenergic agents, ganglionic stimulating and blocking agents, neuromuscular agents, histamines, antihistamines, 5-hydroxytryptamine and antagonists, cardiovascular drugs, antiarrhythmic drugs, antihypertensive agents, vasodilator drugs, diuretics, pesticides (fungicides, antihelminthics, insecticides, ectoparasiticides, etc.), antimalarial drugs, antibiotics, antimetabolites, hormones, vitamins, sugars, thyroid and antithyroid drugs, corticosteroids, insulin, and oral hypoglycemic drugs, as well as other organic materials not normally considered drugs such as tumor cells, bacterial viral and other microbial proteins, toxins, blood proteins, nucleic acids, polysaccharides, lipids, enzymes, cell surface proteins, and their metabolites.

(A drug is any chemical agent that affects living protoplasm. (Goodman & Gilman, *The Pharmacological Basis of Therapeutics,* third Ed., Macmillan, New York (1965)). A narcotic is any agent that produces sleep as well as analgesia).

The non-polymeric compounds of interest will normally be of from about 125 to 2,000 molecular weight. These compounds involve a wide variety of compounds of varying structure, functionality, and physiological properties. The compounds may be acyclic, alicyclic or heterocyclic, both mono- and polycyclic. The heteroatoms involved include oxygen, nitrogen, sulfur, halogen (fluorine, chlorine, bromine and iodine) boron, phosphorous, metal cations of Groups 1A and 2A of the Periodic Chart, and the like.

The functionalities include alcohols, ethers, carboxylic acids, esters and amides, amines (primary, secondary, tertiary and quaternary) halo, mercapto, nitrilo, and the like. Normally, the compounds will be composed solely of carbon, hydrogen, oxygen, sulfur, nitrogen, halogen and phosphorous, particularly carbon, hydrogen, oxygen and nitrogen, and where salts are involved, the appropriate metal counterion or ammonium counterion.

Heterocyclic rings which are present include pyrrole, pyridine, piperidine, indole, thiazole, piperazine, pyran, coumarin, pyrimidine, purine, triazine, imidazole, and the like.

Because of the wide variety of Primary Receptors which can be determined in accordance with the subject assay, the different ligands to which the Primary Receptor binds will be broken down into various, frequently artificial, categories, either by the presence of a particular functionality or ring structure, or because of sharing a particular function or because of being recognized as a class.

The first class of ligands are those having an amino group, either as a heterocyclic member, or as a functionality on an aliphatic chain. These compounds will normally be of from about 110 to 800 molecular weight, more usually of about 125 to 650 molecular weight.

The first group of ligands are the alkaloids and the metabolites of those alkaloids which are ingested. The first group of important alkaloids are alkaloids of the morphine group. Included in this group are morphine, codeine, heroin, morphine glucuronide and the like.

The next group of alkaloids are the cocaine alkaloids, which include, particularly as metabolites, benzoyl ecgonine and ecgonine.

Another group of alkaloids are the cinchone alkaloids which include quinine.

The isoquinoline group of alkaloids includes mescaline.

The benzylisoquinoline alkaloids include papaverine.

The phthalide isoquinoline alkaloids include narcotine, narceine and cotarnine.

The indolopyridocoline alkaloids include yohimbine and reserpine.

The ergot alkaloids include ergotamine and lysergic acid.

Other groups of alkaloids include strychnine alkaloids, pyridine alkaloids, indole alkaloids, piperidine alkaloids, pyrrolizidine alkaloids, and the like.

The alkaloids of primary interest are those which come within the category of drugs of abuse, such as morphine, cocaine, mescaline, and lysergic acid, which may be analyzed for the compound or its metabolite, depending on the physiological fluid which is analyzed for its presence.

A number of synthetic drugs mimic the physiological properties, in part or in whole, of the naturally occurring drugs of abuse. Included among these drugs are methadone, meperidine, amphetamine, methamphetamine, glutethimide, diphenylhydantoin, and drugs which come within the category of benzdiazocycloheptanes, phenothiazines, and barbiturates.

Drugs of interest because of their physiological properties are those which are referred to as catecholamines. Among the catecholamines ar epinephrine, ephredine, L-dopa and norepinephrine.

Another drug of interest is the tranquilizer Meprobamate.

Other compounds of interest are tetrahydrocannabinol, cannabinol, and derivatives thereof, primarily compounds derived from marijuana, synthetic modifications and metabolites thereof.

Another group of compounds of significant interest are the steroids. The steroids include estrogens, gestogens, androgens, adrenocortical hormones, bile acids, cardiotonic glycosides and algycones, saponins and sapogenins.

Another class of compounds are the vitamins, such as vitamin A, the B group, e.g., vitamin $B_1$ and $B_{12}$, E, K, and the like.

Another class of compounds are the sugars, both the mono- and polysaccharides, particularly di- and higher order polysaccharides.

Another class of compounds is the prostaglandins.

Another class of compounds is the amino acids, polypeptides and proteins. Polypeptides usually encompass from about 2 to 100 amino acids units (usually less than about 12,000 molecular weight). Larger polypeptides are arbitrarily called protein and are usually composed of from about 1 to 20 polypeptide chains. Poly (amino acid) will be used as generic to polypeptides and proteins. Of particular interest among amino acids ar the iodosubstituted thyronines, e.g. thyroxine, (tetraiodothyronine) and triiodothyronine.

Another group of compounds are the antibiotics such as penicillin, antinomycin, chloromycetin, and the like.

Another group of compounds are phospholipids.

Individual compounds of interest are serotonin, spermine and phenylpyruvic acid.

Finally, compounds which are pesticides, such as fungicides, insecticides, bactericides, and nematocides, may also have receptors of interest for assaying.

Antibodies of interest in the diagnosis of disease include antibodies involved in systemic lupus erythematosis, such as antibodies to nuclear antigens, such as native or double stranded DNA, nucleoprotein, carbohydrate containing proteins (Sm antigen) and RNA antigens; antibodies to RF factor; antibodies involved with certain bacterial or viral disease, such as subacute bacterial endocarditis, infectious mononucleosis, cytomegalic inclusion disease, syphilis and leprosy; antibodies involved with glomerulonephritis, vasculitis with multisystem involvement, synovitis with joint swelling and pain, polyserositis with pleural effusion and pain, purpura, Raynaud's phenomenon, anemia, deficient exocrine function, lymphoproliferative disorders such as leukemia or lymphoma; antibodies involved with maligant tumors; antibodies involved with cirrhosis; antimitochondrial antibodies; anti-glomerular basement membrane antibodies; anti-parietal cell antibodies; anti-striated muscle antibodies; antibodies active against neurons; antibodies present in pemphigous and bullous pemphigoids $\alpha_1$-anti-chymotrypsin, $\alpha_1$-antitrypsin; and anti(carcinoembryonic antigen).

Reagent

The Reagent will be a molecule having two parts: ligand analog, including the linking group, and Detector Ligand.

While the linking group has been associated with the ligand analog, the linking group could be derived during synthesis of the Reagent from the precursor for the detector Ligand. How the Reagent is synthesized will depend on the groups involved in forming the Reagent. It should be understood that including the linking group as part of the ligand analog is merely a matter of convenience for purpose of discussion.

In most cases, the ligand analog will have a hydrogen of the ligand replaced with a bond to a linking group. As for example, with morphine, the hydrogen of the phenolic hydroxyl can be replaced with a bond to the methylene of an acetyl group. The hydrogen may be replaced by a bond to a linking group which is joined to carbon, either aliphatic or aromatic, oxygen or nitrogen.

In some instances, an oxocarbonyl may serve as the linking site by modifying the oxocarbonyl to an oxime. In other instances, the hydroxyl of a carboxyl group may be replaced to form a linking group, by forming an ester or amide.

Additional alternatives include introducing functionalities, such as hydroxyl functionalities from which ethers can be formed, amino functionalities, from which diazo groups can be formed, and the like.

The significant factor for the ligand analog is that it has sufficient structural similarity to the ligand so as to be recognized by the antibody for the ligand.

For the most part, the ligand analog will have the same or substantially the same structure and charge distribution (spatial and polar organization) as the ligand for a significant, if not major, portion of the molecular surface.

Because of the requirement for steric inhibition due to the presence of one antibody preventing the binding of another antibody to the Reagent, the linking group will normally be relatively short. Usually, the linking group will be substantially less than 25 Å, more usually less than 20 Å, and preferably less than 15 Å. Normally, the linking group will be from about 1.5–10 Å.

The linking group will normally be either a bond or a group of from 1 to 10 atoms, more usually from about 2 to 8 atoms, other than hydrogen. The linking group will normally be composed of carbon, hydrogen, oxygen, sulfur, phosphorous and nitrogen, usually having a nonoxocarbonyl group as part of the linking functionality. (Nonoxocarbonyl is intended to include the amino analogs thereof, e.g. imidate, amidine, etc.)

In many molecules, the molecule may have a plurality of epitopes distant from one another. For example, polypeptides and proteins are known to have a number of different epitopes. When the Detector Ligand is bonded to a polypeptide ligand analog (in this case usually the linking group will have initially been bonded to the Detector Ligand) the Detector Ligand should be within the distances indicated above from an epitope to which an antibody is present in the assay medium. In effect, this molecule will have a plurality of Reagent portions, whereby Primary Receptor (antibody to the ligand epitope) and Secondary Receptor (antibody to the Detector Ligand) are sterically inhibited from being simultaneously bound. For the purposes of this invention, such pairs of ligand analog epitope and detector ligand epitope are considered equivalent to the situation where a ligand analog has a single epitope.

While theoretically, with the exception of the electromagnetic sensitive detector assay, the Detector Ligand may be any ligand other than the ligand specific for the Primary Receptor, as a practical matter the Detector Ligand will normally be a molecule of molecular weight in the range of about 125 to 1,200, more usually 125 to 800. Also, it will usually be preferred that the Detector Ligand will normally not be encountered in the media which are assayed. In addition, the Detector Ligand should have receptors available or allow for the formation of antibodies having high specificity. Another consideration is synthetic convenience, so that the Detector Ligand may be readily bonded to antigenic materials, the ligand analog, and the detector molecule. Finally, the Detector Ligand should be substantially free from interfering physical and chemical properties, such as non-specific binding, susceptibility to oxidation or reduction, susceptibility to chelation and the like. That is, the Detector Ligand should be free of functionalities which will result in interaction with the medium which would change the binding characteristics of the Detector Ligand with its antibody.

As already indicated, a ligand will normally have at least one polar functionality. For the Detector Ligand, two polar functionalities will usually be present and generally not more than about 30 polar functionalities, more usually not more than about four polar functionalities. By polar funtionality is intended a functionality having from one to three heteroatoms, e.g. oxocarbonyl, nonoxocarbonyl, hydroxyl, acetal, hemiacetal, nitro, amino, and the like. Included in the number of heterofunctionalities is the heterofunctionality employed in the linking group. Usually, the Detector Ligand will be cyclic, frequently polycyclic, having from one to five rings, and preferably having at least one ring which is aromatic. The Detector Ligand may be carbocyclic, heterocyclic, aromatic, or have all these groups. As indicated, the requirements for the Detector Ligand are so general, that no particular structure or compound can be specified. In addition, different Detector Ligands may be of particular advantage with different Primary Receptors.

As previously mentioned, one of the advantages of the subject invention is that a single Detectant can be employed in the detection of a wide variety of Primary Receptors. Thus, one can employ a single compound having a radioactive tracer for determining a wide variety of different Primary Receptors. In this manner, one need only store a single radioactive compound for carrying out a wide variety of assays. Since radioactive compounds have relatively short shelf lives, the advantage of using one single radioactive compound for assaying for a wide variety of Primary Receptors is self evident.

With the enzyme assay and the spin label assay, there are numerous synthetic conveniences in having a single Detectant. For example, with the spin label or stable free radical, one of the stable free radicals which is employed is the nitroxide free radical. The nitroxide compounds tend to be relatively water insoluble. If the ligand to the Primary Receptor is also hydrophobic, some technique must be provided for enhancing the hydrophilicity of the resulting ligand-spin label conjugate. By contrast, in the subject invention the Detector Ligand of choice can be hydrophilic. In this manner, the Detector Ligand will render the Reagent and detector molecule water soluble.

Similar considerations are involved in the enzyme process whereby efforts can be made to optimize the properties of a particular enzyme with respect to a particular Primary Receptor, which combination can then serve as a universal detector molecule for a wide variety of Primary Receptors.

In the case where light is the Detectant, the Detector Ligand portion of the Reagent may be a fluorescing group. In choosing the particular fluorescer, a number of general considerations will come into play. The choice of fluorescer will, to a degree, be governed by the ligand. The fluorescer should have light absorption at higher wavelengths than the ligand or ligand-antibody complex. Since one is concerned with a change in the fluorescer emission spectrum as a result of its being bound or unbound to antifluorescer, the emission spectrum of the particular fluorescer compound should be sensitive to the environmental change produced by binding to antifluorescer.

Also, since proteins absorb at a wavelength of about 280nm, the fluorescer should have an absorption maximum above 300 and preferably above 400nm. The molar extinction coefficient should be greatly in excess of 101 l./mole-cm, preferably in excess of $10^5$ l./mole-cm. In addition, a fluorescer of choice will have a large Stokes shift. That is, there should be a substantial spread or difference in wavelengths between the longest wavelength absorption maximum of fluorescer and the shortest wavelength emission maximum of the fluorescer. An additional consideration is that where physiological fluids are concerned, the fluorescer should have minimum non-specific binding to protein.

A number of different fluorescers are described in an article by Brand et al., Fluorescence Probes for Structure, Annual Review of Biochemistry, 41, 843–868 (1972) and Stryer, Science, 162, 526 (1968).

One group of fluorescers having a number of the desirable properties described previously are the xanthene dyes, which include the fluoresceins derived from 3,6-dihydroxy-9-phenyl-xanthhydrol and rosamines and rhodamines, derived from 3,6-diamino-9-phenylxanthydrol. The rhodamines and fluoresceins have a 9-o-carboxyphenyl group, and are derivatives of 9-o-carboxyphenylxanthhydrol.

These compounds are commercially available with substituents on the phenyl group which can be used as the site for bonding or as the bonding functionality. For example, amino and isothiocyanate substituted fluorescein compounds are available.

Another group of fluorescent compounds are the napthylamines, having an amino group in the alpha or beta position, usually alpha position. Included among the naphthylamino compounds are 1-dimethylaminonaphthyl-5-sulfonate, 1-anilino-8-naphthalene sulfonate and 2-p-toluidinyl-6-naphthalene sulfonate. The naphthalene compounds are found to have some non-specific binding to protein, so that their use requires employment in an assay medium where the amount of protein is minimized.

Detectant

With the exception of the electromagnetic radiation sensitive Detector Ligand, the other techniques require the presence of a detector molecule.

In the case of radioimmunoassay, the detector ligand will differ from the ligand by the presence of a radioactive tracer, such as covalently bound tritium, carbon 14, or iodine (atomic weight 125). While other radioactive tracer elements could be used, these particular radioactive elements have found popularity because of synthetic convenience, reasonable shelf life, safety in handling, and the like.

For the spin labeled detector molecule, the detector ligand will be bonded by a linking group, previously described, to a stable free radical group, normally a cyclic nitroxide, disubstituted at the alpha carbon atoms with lower alkyl groups, usually methyl.

For the most part, the spin label compounds will have the following formula:

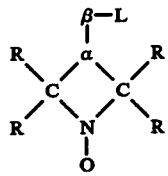

wherein

R is a lower alkyl group of from 1 to 3 carbon atoms, usually methyl;

alpha is a divalent aliphatic group of from 1 to 3 carbon atoms having from 0 to 1 site of ethylenic unsaturation;

beta is a linking group or bond, wherein the linking group is of from 1 to 12 atoms other than hydrogen, usually of from 2 to 6 atoms other than hydrogen, normally having a nonoxocarbonyl group and composed solely of carbon, hydrogen, nitrogen and oxygen, and L is the ligand.

The nitroxide ring will normally have from 5 to 6 annular atoms.

The enzyme detector will have on the average at least about one detector ligand bonded to the enzyme, whereby when antibody is bound to the detector ligand, the enzymatic activity is substantially diminished. The average number of Detector Ligands per enzyme will normally be in the range of about 1 to 25, more usually in the range of about 2 to 20 and preferably in the range of about 1 to 12, usually not exceeding one Detector Ligand per 2,000 molecular weight of enzyme.

The enzymes of significant interest are the hydrolases, lyases and oxidoreductases. Enzymes of particular interest are lysozyme, malate dehydrogenase, glucose-6-phosphate dehydrogenase and amylase. Enzymes of choices have easy detection systems, e.g. spectrophotometric, have large turnover numbers, are relatively stable, and are not present in the materials to be analyzed or may be easily destroyed or removed prior to the assay.

Any detectant system can be employed where an antibody will by binding to the Detector Ligand change a detectable signal.

EXPERIMENTAL

The following examples are offered by way of illustration, and not by way of limitation.

All temperatures are in centigrade unless otherwise indicated.

EXAMPLE 1

Homogeneous enzyme immunoassay for measurement of antiinsulin.

The following reagents were employed (1) carboxymethylmorphine conjugate to insulin, 2 × $10^{-4}$ M in carboxymethylmorphine;

(2) antiinsulin (3) 1 weight percent bovine serum albumin in a buffer, which is 0.55M Tris-HCl pH 7.8 at 30°, 0.003M $MgCl_2$ and $10^{-3}$M sodium azide;

(4) Morphine conjugate to glucose-6-phosphate dehydrogenase having 11.5 haptens on the average per enzyme at a concentration of 0.5 mg/ml;

(5) Antimorphine, 2.1 × $10^{-4}$ M based on binding sites;

(6) Glucose-6-phosphate, as the disodium salt dihydrate, 67.2 mg/ml in buffer; and (7) NAD, Sigma, grade III from yeast, 58.8 mg/ml in water at pH5–6 employing sodium hydroxide.

The assay medium was prepared by initially providing a number of samples employing different amounts of antiinsulin in combination with 0.2 μl of the carboxymethylmorphine insulin conjugate and sufficient of the buffer to bring the total volume to 550 μl. The assay mixture was then incubated for varying times at 37°. To the mixture was then added 0.0308 μl of antimorphine and 0.196 μl of G6PDH-morphine and the solution brought to a volume of 950 μl with buffer. After 20 minutes, 25 μl of G6P and 25 μl of NAD were added to bring the total volume to 1 ml and an aliquot introduced at once into a spectrophotometer. A reading was taken at 5 minutes and 6 minutes after the addition of the enzyme reagents and the following table indicates the optical density change over one minute.

TABLE I

| Antinsulin, μl | Incubation time, hrs | ΔOD/1 min |
|---|---|---|
| 2 | 3.2 | .191 |
|  | 4.2 | .194 |
| 4 | 3.3 | .193 |
|  | 4.3 | .190 |
| 10 | 3.5 | .150 |
|  | 4.5 | .157 |
| 20 | 3.6 | .137 |
|  | 4.5 | .129 |

It is evident from the above results, that one can determine the amount of antiinsulin in a sample by employing standards and following the change in optical density. In fact, the antiinsulin concentration was known to be that 10 μl binds 1.08 × $10^{-10}$ M of insulin, so that by relating the results obtained above, one could determine analogous antiinsulin concentrations. In the above configuration, it is necessary to have sufficient antiinsulin to bind at least about 4.5 × $10^{-11}$ M insulin.

EXAMPLE 2

Spin Label Immunoassay for Detection of Antimorphine

The following reagents were employed:

(1) Buffer 0.013M sodium phosphate, pH 7.4, 0.13M NaCl, $10^{-4}$ M thimerosal;

(2) Antimorphine 2.1 × $10^{-4}$ M in the binding sites;

(3) Antidinitroaniline;

(4) 3-(2',4'-dinitroaniline)-2,2,5,-tetramethylpyrrolidinyl-1-oxyl, $3.48 \times 10^{-5}$ M in 5% methanol in water;

(5) $N^5$-(2',4'-dinitrophenyl) $N^2$-($O^{3''}$-morphinoxyacetyl) lysine, $7.79 \times 10^{-5}$ M in buffer.

The assay was carried out as follows. Various samples were prepared using different amounts of antimorphine. The dinitrophenylmorphine is diluted with buffer to provide a volume of 20 μl having a concentration of $2 \times 10^{-6}$ M of the dinitrophenylmorphine. The mixture was incubated for 0.5 hours and a mixture of preincubated anti(dinitroaniline) and the spin labeled dinitroaniline added, which had concentrations of $2.8 \times 10^{-6}$ M of anti(dinitroaniline) and $3.08 \times 10^{-6}$ M of the spin labeled conjugate. The mixture was scanned in an VARIAN E4 Electron Spin Resonance Spectrophotometer 1 minute after the final addition. The following table indicates the results obtained, reporting the total concentration of antimorphine and the amount of the spin label which was mobilized.

TABLE II

| Final Antimorphine Conc. $\times 10^6$ (binding sites) | % Spin Label Mobilized |
|---|---|
| 10 | 20.2 |
| 3 | 23.3 |
| 1 | 30.8 |

It is evident from the above results that varying degress of mobilization of the spin label can be achieved in proportion to the amount of antibody added. Thus, by employing the steric inhibition which results from employing a reagent as described in the subject invention, where only one antibody can bind at a time, one can assay for varying concentrations of antibodies.

The subject invention provides a versatile sensitive technique for measuring receptors, particularly antibodies. Various available competitive protein binding methods are employed. By using the expedient of a reagent which has at least two epitopic sites, where the binding of one antibody prevents the concomitant binding of a second antibody, one can employ a variety of available reagents for the accurate and quantitative determination of antisera.

Although the foregoing invention has been described in some detail by way of illustration and example for purposes of clarity of understanding, it will be obvious that certain changes and modifications may be practiced within the scope of the appended claims.

What is claimed is:

1. A method for determining the presence of antiligand in an unknown suspected of containing said antiligand which comprises:
    combining in an aqueous medium said unknown, anti(detector ligand) and reagent, wherein said reagent has a pair of epitopes in close proximity so that simultaneous binding of receptors to said pair of epitopes is sterically inhibited, wherein one of said pair of epitopes is recognized by said antiligand and the other said pair of epitopes is recognized by said anti(detector ligand);
    determining by a detectant the amount of remaining unbound anti(detector ligand) or anti(detector ligand) bound to reagent; and
    determining the presence of antiligand by comparing said amount determined with the amount determined with a medium having a known amount of antiligand.

2. A method according to claim 1, wherein said aqueous medium is buffered at a pH in the range of 6 to 9 and said determining is carried out at a temperature in the range of about 15° to 40° C.

3. A method according to claim 2, wherein said detectant includes a detector molecule having an epitopic site recognized by said anti(detector ligand) and a stable free radical group.

4. A method according to claim 3, wherein said stable free radical group is a cyclic nitroxide.

5. A method according to claim 2, wherein said detectant includes a detector molecule having an epitope recognized by said anti(detector ligand) and a radioactive atom.

6. A method according to claim 2, wherein said detectant includes a detector molecule having an epitope recognized by said anti(detector ligand) and an enzyme, wherein said activity of said enzyme is substantially reduced when said epitope recognized by said anti(detector ligand) is bound to antibody.

7. A method according to claim 6, wherein said enzyme is lysozyme, glucose-6-phosphate dehydrogenase, malate dehydrogenase, or amylase.

8. A method for determining the presence of an antiligand in an unknown suspected of containing said antiligand which comprises:
    combining in an aqueous medium buffered at a pH in the range of 6 to 9, said unknown and reagent wherein said reagent has a pair of epitopes in close proximity, so that simultaneous binding of antibodies to said pair of epitopes is sterically inhibited when one of said pair of epitopes is bound by said antiligand or the other of said pair of epitopes is bound by an anti(detector ligand);
    incubating for sufficient time for a steady state to be obtained;
    adding anti(detector ligand); and
    determining by a detectant at a temperature in the range of about 15° and 40° C., the amount of remaining unbound anti(detector ligand) or anti(detector ligand) bound to reagent; and
    determining the presence of antiligand by comparing said amount determined with the amount determined with a medium having a known amount of antiligand.

9. A method according to claim 8, wherein said detectant includes a detector molecule having an epitope recognized by said anti(detector ligand) and a stable free radical group.

10. A method according to claim 9, wherein said stable free radical group is cyclic nitroxide.

11. A method according to claim 8, wherein said detectant includes a detector having an epitope recognized by said anti(detector ligand) and a radioactive atom.

12. A method according to claim 8, wherein said detectant involves a detector molecule having an epitope recognized by said anti(detector ligand) and an enzyme, wherein the activity of said enzyme is substantially reduced when said epitope recognized by said anti(detector ligand) is bound to anti(detector ligand).

13. A method according to claim 12, wherein said enzyme is lysozyme, glucose-6-phosphate dehydrogenase, malate dehydrogenase, or amylase.

* * * * *